United States Patent
Morita (10) Patent No.: US 8,717,045 B2
(45) Date of Patent: May 6, 2014

(54) MICROORGANISM NUMBER MEASUREMENT DEVICE

(75) Inventor: Hidenori Morita, Ehime (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 137 days.

(21) Appl. No.: 13/521,139

(22) PCT Filed: Oct. 14, 2011

(86) PCT No.: PCT/JP2011/005756
§ 371 (c)(1),
(2), (4) Date: Jul. 9, 2012

(87) PCT Pub. No.: WO2012/053169
PCT Pub. Date: Apr. 26, 2012

(65) Prior Publication Data
US 2012/0280701 A1    Nov. 8, 2012

(30) Foreign Application Priority Data

Oct. 20, 2010  (JP) ................................. 2010-235344
Oct. 20, 2010  (JP) ................................. 2010-235345

(51) Int. Cl.
*G01R 27/08*    (2006.01)

(52) U.S. Cl.
USPC ........... 324/691; 324/439; 324/722; 324/638; 324/639; 422/68.1; 422/73; 422/82.01; 436/150; 436/69; 436/523; 436/10

(58) Field of Classification Search
USPC ......... 324/691, 439, 722, 600, 633, 638, 637, 324/639, 158.1; 422/68.1, 73, 82.01; 436/150, 69, 523, 10
See application file for complete search history.

(56) References Cited

U.S. PATENT DOCUMENTS

| 4,433,299 | A | * | 2/1984 | Kawai et al. .................. 204/549 |
| 5,254,461 | A | * | 10/1993 | Rohrback et al. .......... 205/777.5 |
| 6,846,639 | B2 | * | 1/2005 | Miles et al. .................... 435/7.1 |

(Continued)

FOREIGN PATENT DOCUMENTS

| JP | 63286754 A | 11/1988 |
| JP | 2001311710 A | 11/2001 |

(Continued)

OTHER PUBLICATIONS

International Application Serial No. PCT/JP2011/005756, International Search Report mailed Dec. 27, 2011, 4 pgs.

*Primary Examiner* — Tung X Nguyen
*Assistant Examiner* — Thang Le
(74) *Attorney, Agent, or Firm* — RatnerPrestia (57) ABSTRACT

A microorganism number-measuring apparatus includes: measurement container including measurement liquid; rotary driver; bacteria-collection signal generator; measurement signal generator; output amplifier for amplifying outputs of signal generators and; I/V amplifier; impedance measuring unit for measuring impedance of liquid; microorganism number-computing unit for computing the number of microorganisms present in liquid; solution conductivity-computing unit for computing conductivity of liquid; and warm-up section for warming up at least one of I/V amplifier and output amplifier. Warm-up section computes a warm-up signal based on the conductivity computed by conductivity-computing unit. Warm-up section computes the warm-up signal having a current the same in magnitude as that flowing through measurement electrode by using the measured solution conductivity, and applies the signal to at least one of I/V amplifier and output amplifier.

4 Claims, 6 Drawing Sheets

(56) References Cited

U.S. PATENT DOCUMENTS

| | | |
|---|---|---|
| 6,909,269 B2 * | 6/2005 | Nagai et al. .................. 324/71.4 |
| 8,004,291 B2 * | 8/2011 | Waki .............................. 324/692 |
| 2003/0098690 A1 * | 5/2003 | Higo .............................. 324/439 |
| 2008/0012577 A1 * | 1/2008 | Potyrailo et al. ............... 324/633 |
| 2009/0085588 A1 * | 4/2009 | Papadakis ...................... 324/722 |
| 2009/0223824 A1 * | 9/2009 | Oouchi ........................... 204/545 |
| 2010/0075340 A1 * | 3/2010 | Javanmard et al. ............ 435/7.1 |

FOREIGN PATENT DOCUMENTS

| | | |
|---|---|---|
| JP | 2005241404 A | 9/2005 |
| JP | 2009207431 A | 9/2009 |
| WO | WO-2009113250 A1 | 9/2009 |
| WO | WO-2009128233 A1 | 10/2009 |

* cited by examiner

MICROORGANISM NUMBER MEASUREMENT DEVICE

This Application is a U.S. National Phase Application of PCT International Application No. PCT/JP2011/005756.

TECHNICAL FIELD

The present invention relates to a microorganism number-measuring apparatus, in particular to a microorganism number-measuring apparatus for measuring the number of microorganisms present in an oral cavity.

BACKGROUND ART

First, a configuration of a conventional microorganism number-measuring apparatus is described.

The conventional microorganism number-measuring apparatus includes: a measurement container, a rotary driver, a bacteria-collection signal generator, a measurement signal generator, an output amplifier, an I/V (current/voltage conversion) amplifier, an impedance measuring unit, a microorganism number-computing unit, and a solution conductivity-computing unit.

The measurement container is such that a measurement electrode is disposed in a measurement liquid inside the container, in an immersed state in the liquid. The rotary driver rotationally drives the measurement container. The bacteria-collection signal generator feeds an alternate-current bacteria-collection signal to the measurement electrode. The measurement signal generator feeds a measurement signal to the measurement electrode. The output amplifier is coupled with an output of the measurement signal generator and with an output of the bacteria-collection signal generator.

Moreover, the I/V amplifier is coupled with an output of the output amplifier via the measurement electrode. The impedance measuring unit is coupled with the I/V amplifier to measure impedance of the measurement liquid. The microorganism number-computing unit is coupled with the impedance measuring unit. The solution conductivity-computing unit is coupled with the impedance measuring unit.

In the conventional microorganism number-measuring apparatus, the microorganism number-computing unit computes the number of microorganisms based on the impedance measured by the impedance measuring unit (see Patent Literature 1, for example).

When using such the conventional microorganism number-measuring apparatus to measure the number of microorganisms (bacteria) present in an oral cavity, variations in measurement accuracy appear due to variations in electric drifts which occur in a system of measurement.

Of the electric drifts of the system of measurement, it is a particularly problematic drift that occurs in the I/V amplifier for converting an electric current flowing through the measurement electrode into a voltage. In the I/V amplifier, heat associated with use is generated to cause a large drift in the system of measurement. Variations in the drift appear at a certain rate corresponding to the magnitude of the drift. The variations in the drift will possibly provide adverse effects on measurement accuracy.

CITATION LIST

Patent Literature

Patent Literature 1: Japanese Patent Unexamined Publication No. 2009-207431

SUMMARY OF THE INVENTION

The present invention is made in view of the aforementioned problems, and an objective of the invention is to provide further increased measurement accuracy.

The invention is intended to provides a microorganism number-measuring apparatus that includes: a measurement container including a measurement liquid in which a measurement electrode is disposed in an immersed state; a rotary driver for rotationally driving the measurement container; a bacteria-collection signal generator for feeding a bacteria-collection signal to the measurement electrode; and a measurement signal generator for feeding a measurement signal to the measurement electrode. Moreover, the apparatus includes: an output amplifier for amplifying an output of the measurement signal generator and an output of the bacteria-collection signal generator; an I/V amplifier coupled with an output of the output amplifier via the measurement electrode; and an impedance measuring unit coupled with the I/V amplifier so as to measure impedance of the measurement liquid. The apparatus also includes: a microorganism number-computing unit coupled with the impedance measuring unit so as to compute the number of microorganisms in the measurement liquid; a solution conductivity-computing unit coupled with the impedance measuring unit so as to compute a solution electric conductivity of the measurement liquid; and a warm-up section for warming up at least one of the I/V amplifier and the output amplifier. Moreover, the solution conductivity-computing unit is coupled with the warm-up section, and an output of the warm-up section is coupled with at least one of the I/V amplifier and the output amplifier, via a warm-up switch. In a measurement setup mode, the solution conductivity-computing unit measures the solution conductivity of the measurement liquid, and the warm-up section computes a warm-up signal by using the measured solution conductivity, with the warm-up signal having an electric current equal in amount to a current flowing through the measurement electrode. The warm-up section performs a warm-up operation by applying the warm-up signal to at least one of the I/V amplifier and the output amplifier.

DESCRIPTION OF EMBODIMENTS (First Exemplary Embodiment)

Hereinafter, a description of a first embodiment of the present invention will be made, with reference to the drawings.

Figure 1:
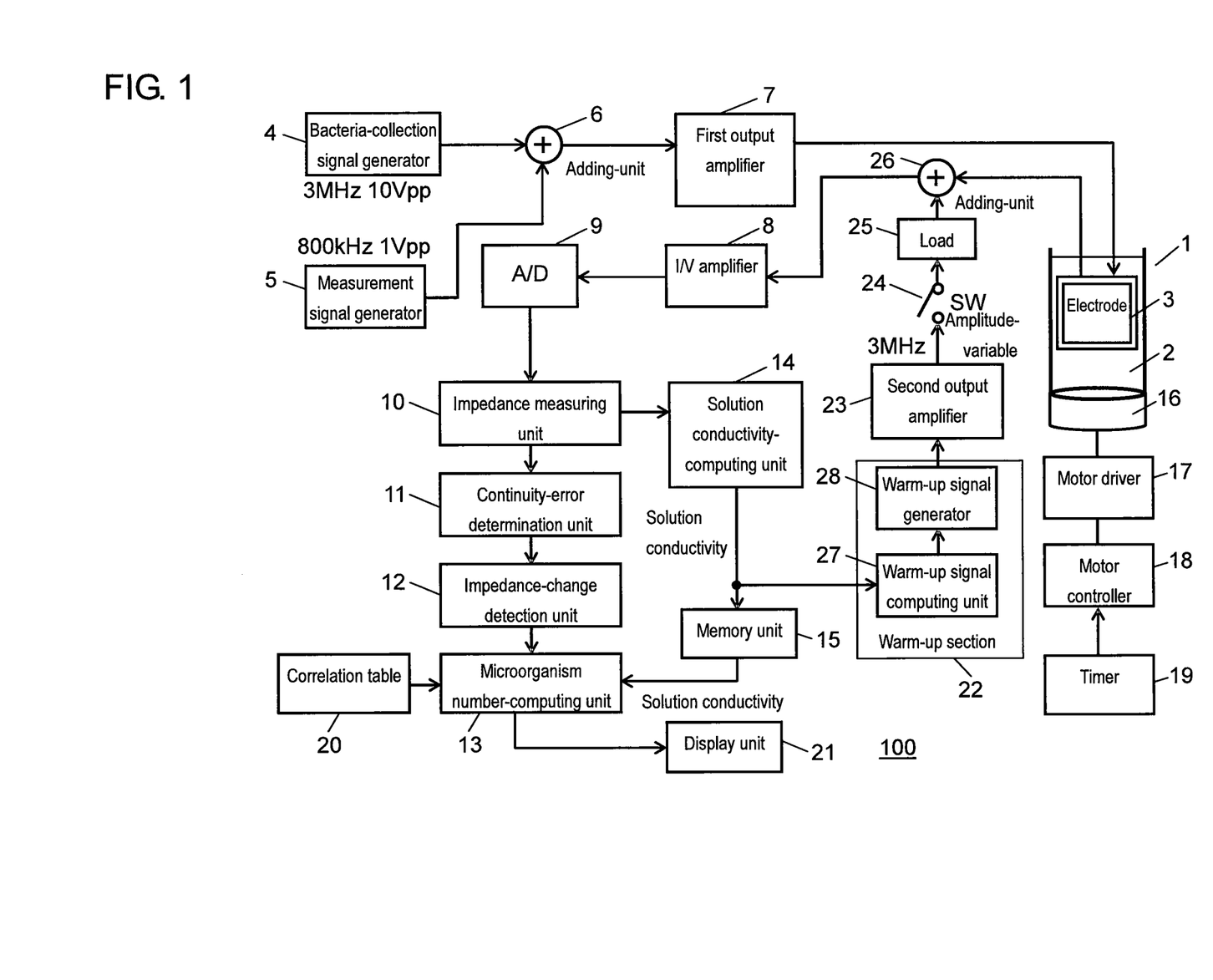
FIG. 1 is a block diagram of a configuration of a microorganism number-measuring apparatus according to a first embodiment of the present invention.

FIG. 1 is a block diagram of a configuration of microorganism number-measuring apparatus 100 according to the first embodiment of the invention.

Microorganism number-measuring apparatus 100 includes: measurement electrode 3; measurement container 1; motor 16 serving as a rotary driver; bacteria-collection signal generator 4; measurement signal generator 5; first output amplifier 7; I/V amplifier 8; impedance measuring unit 10; microorganism number-computing unit 13; solution conductivity-computing unit 14; and warm-up section 22.

Measurement container 1 includes measurement liquid 2. Measurement electrode 3 is disposed in the container. Motor 16 rotationally drives measurement container 1. Bacteria-collection signal generator 4 feeds a bacteria-collection signal to measurement electrode 3. Measurement signal generator 5 feeds a measurement signal to measurement electrode 3.

First output amplifier 7 amplifies an output of measurement signal generator 5 and an output of bacteria-collection signal generator 4. I/V amplifier 8 is coupled with an output of first output amplifier 7 via measurement electrode 3. Impedance measuring unit 10 is coupled with I/V amplifier 8 so as to measure impedance of measurement liquid 2.

Microorganism number-computing unit 13 is coupled with impedance measuring unit 10 so as to compute the number of microorganisms present in measurement liquid 2. Solution conductivity-computing unit 14 is coupled with impedance measuring unit 10 so as to compute electric conductivity of measurement liquid 2.

Then, warm-up section 22 applies a warm-up signal to I/V amplifier 8 so as to perform warm-up of I/V amplifier 8. Warm-up section 22 computes the warm-up signal based on the electric conductivity computed in solution conductivity-computing unit 14.

Now, a more detailed description of the configuration of microorganism number-measuring apparatus 100 will be made.

Measurement container 1 is a cylinder-shaped container, the top face of which is opened. In the inside of measurement container 1, measurement liquid 2 is accommodated. Into measurement liquid 2, the microorganisms are released which have been collected from the inside of an oral cavity by using a sampling tool such as a cotton swab (not shown). In measurement liquid 2, measurement electrode 3 is disposed in an immersed state.

Measurement electrode 3 is such that comb-like electrodes are disposed opposite to each other with a predetermined spacing, and the electrode described in Patent Literature 1, can be used, for example. Measurement electrode 3 is coupled with bacteria-collection signal generator 4 and measurement signal generator 5, via adding-unit 6 and first output amplifier 7. Bacteria-collection signal generator 4 feeds an alternate-current bacteria-collection signal (e.g. 3 MHz, 10 Vpp) to measurement electrode 3. Measurement signal generator 5 feeds an alternate-current measurement signal (e.g. 800 kHz, 1 Vpp) to measurement electrode 3.

Adding-unit 6 adds the alternate-current bacteria-collection signal that is fed from bacteria-collection signal generator 4 and the alternate-current measurement signal that is fed from measurement signal generator 5. The added signal is fed to measurement electrode 3 via first output amplifier 7.

Measurement electrode 3 is coupled with microorganism number-computing unit 13, via I/V amplifier 8, A/D converter 9, impedance measuring unit 10, continuity-error determination unit 11, and impedance-change detection unit 12. Functions of continuity-error determination unit 11 and impedance-change detection unit 12 will be described later.

Note that, between I/V amplifier 8 and A/D converter 9, a lowpass filter (not shown) is disposed so as to feed only a signal of e.g. 800 kHz to impedance measuring unit 10.

Impedance measuring unit 10 is coupled with solution conductivity-computing unit 14. Solution conductivity-computing unit 14 is coupled with memory unit 15. Data stored in memory unit 15 are fed to microorganism number-computing unit 13, which are to be used in computing the number of the microorganisms.

Under measurement container 1, motor 16 is attached via a container holder (not shown). Measurement container 1 is rotationally driven by motor 16. Motor 16 is subjected to rotation control by motor controller 18 via motor driver 17.

Motor controller 18 drives motor 16 to rotate at e.g. 600 rpm. Incidentally, motor controller 18 is coupled with timer 19.

Microorganism number-computing unit 13 computes the number of the microorganisms by using correlation table 20 coupled with microorganism number-computing unit 13, and then displays the thus-computed number of the microorganisms on display unit 21.

Moreover, in the embodiment, the output side of solution conductivity-computing unit 14 is coupled with warm-up section 22 that performs the warm-up of I/V amplifier 8. An output of warm-up section 22 is coupled with I/V amplifier 8 via second output amplifier 23, warm-up switch 24, load 25, and adding-unit 26.

Warm-up section 22 includes: warm-up signal computing unit 27, and warm-up signal generator 28 that is coupled with the output side of the warm-up signal computing unit.

Next, a description will be made of an operation of microorganism number-measuring apparatus 100 according to the embodiment.

Figure 2:
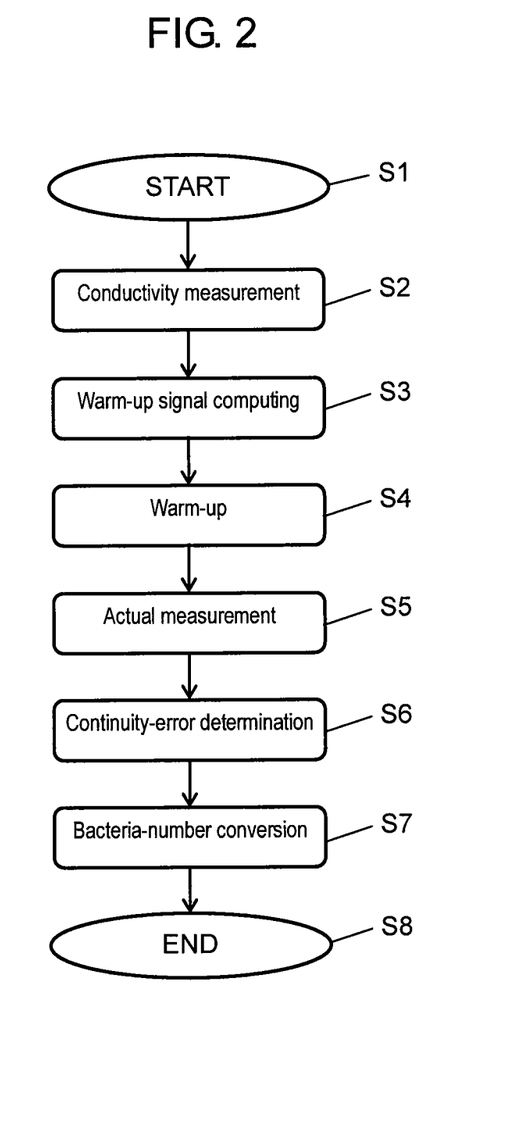
FIG. 2 is a flowchart of an operation of the microorganism number-measuring apparatus according to the embodiment of the invention.

FIG. 2 is a flowchart showing the operation of the microorganism number-measuring apparatus according to the embodiment of the invention.

First, the operation of microorganism number-measuring apparatus 100 is started with the state where, in measurement liquid 2, the microorganisms are released which have been collected from the inside of an oral cavity by using a sampling tool such as a cotton swab (not shown) (S1).

On this occasion, motor controller 18 drives motor 16 to rotate at e.g. 600 rpm, which causes measurement container 1 to rotate at 600 rpm via the container holder (not shown). The rotation of measurement container 1 provides a rotational slewing force for measurement liquid 2 to form a whirlpool. The whirlpool conveys the microorganisms, which have been released in measurement liquid 2, toward measurement electrode 3.

On this occasion, warm-up switch 24 is in an open state where second output amplifier 23 is not coupled with load 25.

Next, solution conductivity-computing unit 14 measures a solution electric conductivity of measurement liquid 2 (S2). Note that, three steps from S2 to S4 configure a measurement setup mode. The measurement setup mode is one where a preparation is made for an actual measurement to be performed in step S5.

In step S2, firstly, measurement signal generator 5 feeds a measurement signal (e.g. 800 kHz, 1 Vpp) to measurement electrode 3 via adding-unit 6 and first output amplifier 7.

Solution conductivity-computing unit 14 computes the solution electric conductivity by using the measured data of the impedance of measurement liquid 2, which have been measured by impedance measuring unit 10. Solution conductivity-computing unit 14 stores the thus-computed solution conductivity in memory unit 15.

In the embodiment, the magnitude of an electric drift occurring in a system of measurement is determined depending on a state of measurement liquid 2 (specifically, on solution conductivity of measurement liquid 2).

Here, the reason of this is described. The magnitude of the drift in the system of measurement is determined depending on an electric current (i.e. on heat associated with the current) that flows through the system of measurement. In the measurement of the number of microorganisms in the embodiment, the microorganisms are collected with a sampling tool such as a cotton swab from the inside of the oral cavity of a patient. When collecting the microorganisms, saliva is taken together with the microorganisms. The quality and quantity of the saliva causes the solution conductivity (i.e. the ease with which an electric current flows) of measurement liquid 2 to change. Therefore, the current flowing through the system of measurement changes depending on the state of measurement liquid 2. For this reason, the magnitude of the drift in the system of measurement is caused to change depending on the state of measurement liquid 2 (specifically, on the solution conductivity of measurement liquid 2).

Figure 3:
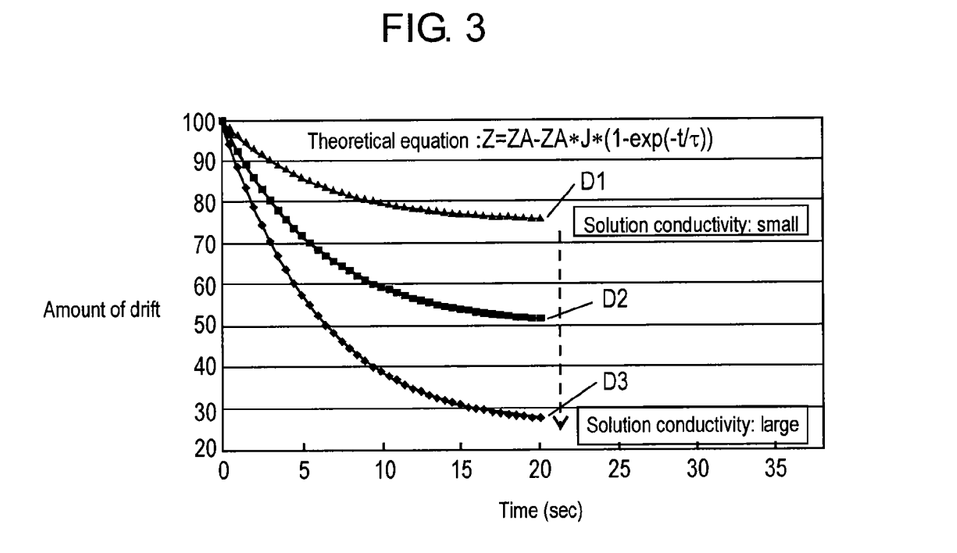
FIG. 3 is a graph illustrating a relation between states of a measurement liquid (a solution electric conductivity of the measurement liquid) and the magnitude of drifts in a system of measurement according to the embodiment of the invention.

FIG. 3 is a graph illustrating the relation between states of measurement liquid 2 (solution electric conductivities of the measurement liquid) and the magnitude of drifts in the system of measurement according to the embodiment of the invention. Note that, here, the magnitude of the drifts is derived by means of the theoretical equation described below. Moreover, the magnitude of the drifts, referred to here, is the amount of the change in impedance from initial impedance to stable state impedance.

$$Z = ZA - ZA \times J \times (1 - \exp(-t/\tau)),$$

where

Z: impedance of the system of measurement,

ZA: initial impedance of the system of measurement (e.g. 100 for the example in FIG. 3), J: a coefficient that determines the magnitude of a drift caused by heat generation (the larger the solution conductivity, the larger the value of J is), and $\tau$: a time constant that determines the rate of a change in impedance, i.e. a specific time constant determined depending on the system of measurement (e.g., curve D2 is the case where ZA:100, J:0.5, and $\tau$:6).

The theoretical equation described above is one that expresses a change in impedance (Z) of the system of measurement. The theoretical equation expresses the phenomenon that the impedance changes exponentially due to temperature rise caused by heat generation, from the initial impedance to the stable state impedance.

In the theoretical equation, the magnitude of the drift is determined from coefficient (J) that determines the magnitude of the drift caused by heat generation. Moreover, the rate of the change in impedance is determined from time constant ($\tau$).

It is noted that the magnitude of the drift is expressed as equal to initial impedance (ZA) subtracted by impedance (Z) of the system of measurement. That is, the drift is expressed as $ZA \times J \times (1-\exp(-t/\tau))$.

FIG. 3 shows the magnitude of the drifts of the system of measurement when using three classes of measurement liquids 2 having solution electric conductivities (D1 to D3). Note that these solution conductivities satisfy the relation of D1<D2<D3.

As shown in FIG. 3, with any of the solution conductivities, the drifts settle into stable states with time. The stable-state drifts are determined for the respective solution conductivities (D1 to D3).

More specifically, when the solution conductivity of measurement liquid 2 is small, the current flowing through measurement electrode 3 becomes small, resulting in the small current flowing through the system of measurement. This reduces the amount of the heat generated in the system of measurement, which in turn reduces the magnitude of the drift (the amount of the change in impedance, from the initial impedance to the stable state impedance).

In contrast, when the solution conductivity of measurement liquids 2 is large, the current flowing through measurement electrode 3 becomes large, resulting in the large current flowing through the system of measurement. This increases the amount of heat generated in the system of measurement, which in turn increases the magnitude of the drift (the amount of the change in impedance, from the initial impedance to the stable state impedance).

Based on these relations, in the embodiment, step S2 is configured to measure the solution conductivity of measurement liquid 2, followed by the subsequent step to determine the amount of the current based on the measured solution conductivity. The thus-determined amount of the current, in turn, determines the magnitude of the electric drift (the amount of the change in impedance, from the initial impedance to the stable state impedance) of the system of measurement.

It is noted that, in the embodiment, of the electric drifts of the system of measurement, noteworthy is the drift of I/V amplifier 8 which converts the current flowing through measurement electrode 3 into a voltage. In I/V amplifier 8, heat associated with use is generated to cause a large drift in the system of measurement. Corresponding to the magnitude of the drift, variations in measured values are caused at a certain rate.

After step S2, warm-up signal computing unit 27 of warm-up section 22 computes the warm-up signal for warming up I/V amplifier 8 (S3).

Warm-up signal computing unit 27 computes the warm-up signal with the same current in magnitude as that flows through measurement electrode 3 during the measurement. This allows the warm-up of the system of measurement to the extent that equals the magnitude of the drift corresponding to the solution electric conductivity determined in step S2.

The warm-up signal is one which causes I/V amplifier 8 configuring the system of measurement to generate heat in the same state as during the measurement. Therefore, when the warm-up signal is set to an alternating current of 3 MHz equal in frequency to the bacteria-collection signal, warm-up signal computing unit 27 is expected to compute the amplitude of the warm-up signal.

In order to determine the amplitude, warm-up signal computing unit 27 starts by determining the magnitude of a current that is to flow through measurement electrode 3 during the actual measurement (during application of the bacteria-collection signal), based on the solution conductivity determined in step S2.

Next, the warm-up signal computing unit computes the amplitude of the warm-up signal such that the current flowing through I/V amplifier 8 during application of the warm-up signal is substantially equal in amount to the current that is to flow through I/V amplifier 8 during the measurement. Note that the amplitude can be appropriately computed and determined in consideration of the magnitude of load 25, through which the warm-up signal flows upon applied from warm-up section 22.

This is because as follows: When applying the warm-up signal, the current thereof is caused to flow through load 25 without flowing through measurement electrode 3. Incidentally, the magnitude of the current which is to flow through measurement electrode 3 changes depending on the solution conductivity. Therefore, in order to cause the current to flow through load 25, with the current being the same in magnitude as the thus-changing current, warm-up signal computing unit 27 computes the amplitude of the warm-up signal in consideration of the magnitude of load 25.

After step S3, warm-up section 22 performs the warm-up (S4).

Here, warm-up signal generator 28 performs the warm-up of I/V amplifier 8, by using the warm-up signal formed in step S3. On this occasion, the warm-up is preferably performed in the state where measurement electrode 3 is not applied with the bacteria-collection signal (3 MHz, 10 Vpp).

During the warm-up, in case of applying the bacteria-collection signal to measurement electrode 3 and having collected bacteria, the microorganisms adhere to measurement electrode 3 and remain there even if the application of the bacteria-collection signal is halted. This possibly causes a decrease in measurement accuracy.

For this reason, in the embodiment, it is configured that warm-up switch 24 is disposed in the I/V amplifier 8 side of measurement electrode 3. With this configuration, it is only during the warm-up that warm-up switch 24 can be turned ON to apply the warm-up signal to I/V amplifier 8 via second output amplifier 23, load 25, and adding-unit 26. That is, since the warm-up signal as well as the bacteria-collection signal has the ability of collecting bacteria, it is configured that the warm-up signal is not applied to measurement electrode 3, by means of warm-up switch 24 being turned ON during the warm-up. Accordingly, there is no decrease in measurement accuracy caused by the application of the warm-up signal to measurement electrode 3.

When performing the warm-up, firstly, warm-up signal generator 28 starts by generating a warm-up voltage (3 MHz) with the amplitude of the load voltage that has been computed in step S3.

Next, warm-up switch 24 is turned ON such that warm-up section 22 feeds the warm-up signal (3 MHz). The warm-up signal is applied to I/V amplifier 8 via second output amplifier 23, warm-up switch 24, load 25, and adding-unit 26. This causes I/V amplifier 8 to generate heat in the same state as during the measurement. In step S4, the warm-up is continuously performed for a certain period of time (e.g. 10 seconds).

With this configuration, for a period until the measurement is started, it is possible to cause I/V amplifier 8 to generate heat in the same state of the drift as during the measurement. Then, in the actual measurement, the measurement can be performed through the use of I/V amplifier 8 having generated heat sufficiently, which thereby reduces the drift caused by heat generation during the measurement. Accordingly, this allows a reduction in variations in the drift, resulting in a further increase in measurement accuracy.

Following step S4, the actual measurement for determining the number of microorganisms is then performed (S5).

In step S5, firstly, warm-up switch 24 is turned OFF to halt the warm-up voltage fed from warm-up section 22. Next, adding-unit 6 adds the bacteria-collection signal voltage generated by bacteria-collection signal generator 4 and the measurement signal voltage generated by measurement signal generator 5. The thus-added voltage is fed to measurement electrode 3 via first output amplifier 7.

The application of the bacteria-collection signal voltage to measurement electrode 3 generates a dielectrophoretic force which, at measurement electrode 3, collects the microorganisms present in measurement liquid 2. Then, capacitance appears corresponding to the quantity of the microorganisms collected at measurement electrode 3. The value of the capacitance is, that is, the value of the impedance to be measured by impedance measuring unit 10.

In step S6 following step S5, continuity-error determination unit 11 determines continuity of the impedance that has been continuously measured by impedance measuring unit 10, and excludes the impedance values as errors if the values are determined to have no continuity. On the other hand, when all the impedance values have continuity, continuity-error determination unit 11 determines that all the impedance values are correct ones.

In step S7 following step S6, impedance-change detection unit 12 computes the amount of the change in impedance (the amount of the change in capacitance). Based on the inclination of the change in impedance and on the data stored in correlation table 20, microorganism number-computing unit 13 computes the number of the microorganisms. Note that the change in impedance to be used here has been corrected by using the solution electric conductivity of measurement liquid 2 that is stored in memory unit 15, before microorganism number-computing unit 13 computes the number of the microorganisms.

Then, the value thus-computed by microorganism number-computing unit 13 is displayed on display unit 21, by the unit of 1×10 to the 6th power CFU/ml (CFU is the number of microorganisms forming a colony), for example. This completes the measurement (S8).

Figure 4:
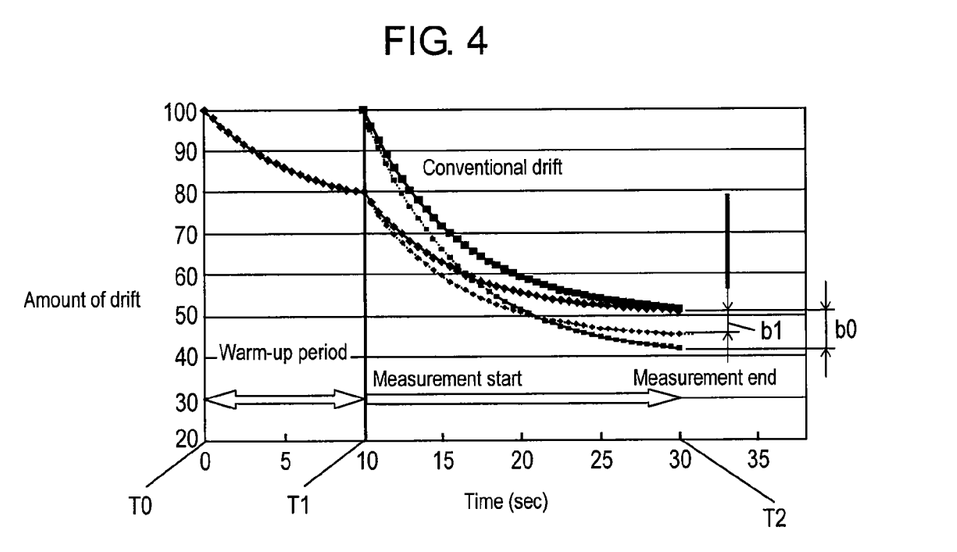
FIG. 4 is a graph illustrating variations in the drifts during the operation of the microorganism number-measuring apparatus according to the first embodiment of the invention.

FIG. 4 is a graph illustrating variations in the drifts during the operation of microorganism number-measuring apparatus 100 according to the first embodiment of the invention. FIG. 4 shows the changes with time in magnitude of the drifts of the system of measurement, which are derived using the theoretical equation under a certain condition, for both the case where warm-up is performed and the case where no warm-up is performed.

As described above, in I/V amplifier 8, heat associated with use is generated. The heat causes a large drift of the system of measurement.

As shown in FIG. 4, the drifts settle into stable states with time in any of the cases. Associated with the drifts, variations in the measured values appear at a certain rate. Accordingly, the variations become large as the magnitude of the drifts (the amounts of the changes in impedance, from the initial impedance to the stable state impedance) becomes large. The variations possibly affect measurement accuracy.

A more specific description is made. As shown in FIG. 4, in the conventional cases, the drifts change for the period from actual-measurement starting time T1 (the amount of the drift: 100) to measurement ending time T2 (the amount of the drift: approximately 50). The amounts of the changes are so large that a large variation (b0) appears in the changes in the drifts, even in the same conditions.

In contrast, in microorganism number-measuring apparatus 100 according to the embodiment, the warm-up described in steps S2 to S4 is performed for the period of time from T0 to T1 (the preheating warm-up period), before starting the actual measurement. Through the warm-up, I/V amplifier 8 is caused to generate heat before the measurement, in the same state as during the measurement.

Accordingly, in the cases of FIG. 4, the amounts of the drifts can be reduced to 80 at actual-measurement starting time T1.

Therefore, compared with the case where the no warm-up is performed, the changes in the amounts of the drifts can be made small for the period from actual-measurement starting time T1 (the amount of the drift: 80) to measurement ending time T2 (the amount of the drift: 50), which allows a reduced variation (b1) in the drifts.

Moreover, in microorganism number-measuring apparatus 100 according to the embodiment, the warm-up is performed using the warm-up signal that has been computed by warm-up section 22. Therefore, it is possible to accurately predict the state of the drift (the ending point of the drift) at the time when the warm-up is finished.

Therefore, in the embodiment, the ending point of the drift caused by the warm-up can be set as a starting point of the drift to be caused during the measurement. Accordingly, in the measurement, microorganism number-computing unit 13 is allowed to perform an appropriate correction corresponding to the drift-changing, which thereby allows an increase in measurement accuracy.

As a result, use of microorganism number-measuring apparatus 100 according to the embodiment permits a further increase in measurement accuracy.

(Second Exemplary Embodiment)

Next, a description of a second embodiment of the present invention will be made.

Figure 5:
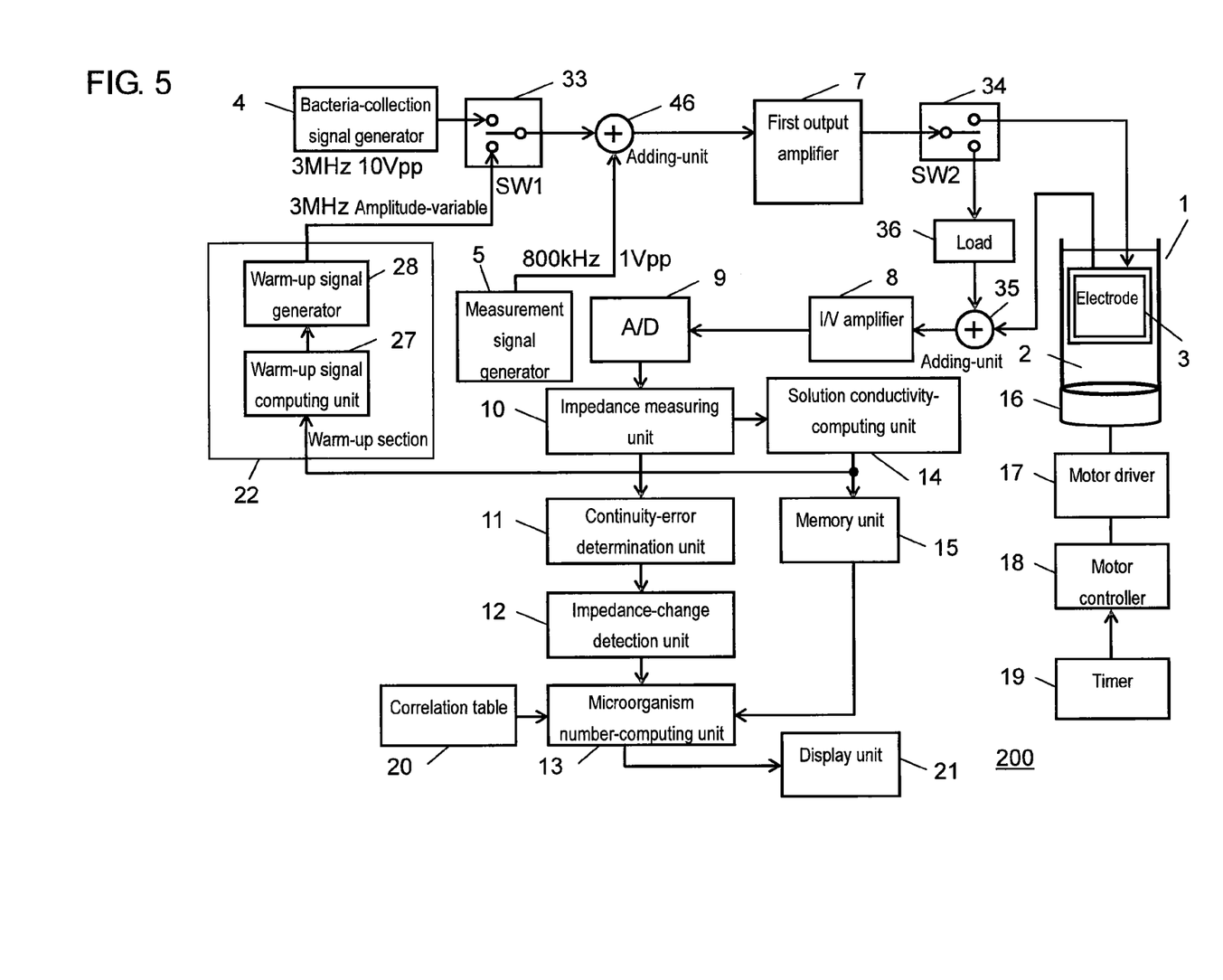
FIG. 5 is a block diagram of a configuration of a microorganism number-measuring apparatus according to a second embodiment of the invention.

FIG. 5 is a block diagram of a configuration of microorganism number-measuring apparatus 200 according to the second embodiment of the invention.

A difference of microorganism number-measuring apparatus 200 according to the embodiment from microorganism number-measuring apparatus 100 described in the first embodiment, is in that warm-up section 22 warms up first output amplifier 7 and I/V amplifier 8.

Warm-up section 22 is coupled with the output side of solution conductivity-computing unit 14. Moreover, an output of warm-up section 22 is coupled with first warm-up switch 33.

First warm-up switch 33 is coupled between bacteria-collection signal generator 4 and adding-unit 46. First warm-up switch 33 switches over between an input fed from bacteria-collection signal generator 4 and an input fed from warm-up section 22, and feeds it to adding-unit 46. Adding-unit 46 adds the output of first warm-up switch 33 and an output of measurement signal generator 5, and feeds the added result to first output amplifier 7.

First output amplifier 7 is coupled with second warm-up switch 34. Second warm-up switch 34 selectively feeds an output of first output amplifier 7 to measurement electrode 3 or load 36. Load 36 is coupled between second warm-up switch 34 and adding-unit 35. Adding-unit 35 adds an output of measurement electrode 3 and an output of load 36, and feeds the added result to I/V amplifier 8.

Other constituent elements, the same as those of microorganism number-measuring apparatus 100 described in the first embodiment, are designated by the same numerals and symbols, and their explanations are omitted.

In the embodiment, the output side of solution conductivity-computing unit 14 is coupled with warm-up unit 22 that performs the warm-up of first output amplifier 7 and I/V amplifier 8. Moreover, first warm-up switch 33 is disposed to selectively couple an output of warm-up unit 22 or an output of bacteria-collection signal generator 4 to the input side of first output amplifier 7.

In addition, second warm-up switch 34 is disposed to selectively couple the output of first output amplifier 7 to measurement electrode 3 or I/V amplifier 8. One of the outputs of second warm-up switch 34 is coupled with measurement electrode 3, and the other is coupled with I/V amplifier 8 via load 36 and adding-unit 35. Therefore, the output side of first output amplifier 7 is selectively coupled with measurement electrode 3 or I/V amplifier 8 by means of second warm-up switch 34.

Moreover, as shown in FIG. 5, measurement electrode 3 is coupled with I/V amplifier 8 via adding-unit 35.

Note that it is the same as in the first embodiment that warm-up unit 22 is configured with warm-up signal computing unit 27 and warm-up signal generator 28 coupled with the output side of the computing unit.

An operation of thus-configured microorganism number-measuring apparatus 200 will be described in detail, with reference to the flowchart of FIG. 2. Although there is a commonality in operation between microorganism number-measuring apparatus 200 and microorganism number-measuring apparatus 100 described in the first embodiment, their operations in each step are sometimes different from each other.

First, the operation of microorganism number-measuring apparatus 200 is started with the state where, in measurement liquid 2, the microorganisms are released which have been collected from the inside of an oral cavity by using a sampling tool such as a cotton swab (not shown) (S1).

On this occasion, motor controller 18 drives motor 16 to rotate at e.g. 600 rpm, which causes measurement container 1 to rotate at 600 rpm via the container holder (not shown). The rotation of measurement container 1 provides a rotational slewing force for measurement liquid 2 to form a whirlpool. The whirlpool conveys the microorganisms, which have been released in measurement liquid 2, toward measurement electrode 3.

Next, solution conductivity-computing unit 14 measures the solution electric conductivity of measurement liquid 2 (S2). Note that, three steps from S2 to S4 configure a measurement setup mode, which is the same as in the first embodiment. The measurement setup mode is one where a preparation is made for an actual measurement to be performed in step S5.

In step S2, firstly, second warm-up switch 34 is operated to select the measurement electrode 3 side such that the output of first output amplifier 7 is coupled with measurement electrode 3.

Next, measurement signal generator 5 supplies a measurement signal (e.g. 800 kHz, 1 Vpp) to measurement electrode 3 via adding-unit 46, first output amplifier 7, and second warm-up switch 34.

Solution conductivity-computing unit 14 computes the solution electric conductivity by using the measured data of the impedance of measurement liquid 2, which have been measured by impedance measuring unit 10. Solution conductivity-computing unit 14 stores the thus-computed solution conductivity in memory unit 15.

In the embodiment as well, the magnitude of an electric drift that occurs in a system of measurement is determined depending on a state of measurement liquid 2 (specifically, on solution conductivity of measurement liquid 2). The reason of this is the same as that described in the first embodiment with reference to FIG. 3.

In the embodiment, of the electric drifts of the system of measurement, it is the drifts of first output amplifier 7 and I/V amplifier 8 that are taken into consideration, where first output amplifier 7 is fed with a bacteria-collection signal (3

MHz, 10 Vpp) generated by bacteria-collection signal generator 4, and I/V amplifier 8 converts the current flowing through measurement electrode 3 into a voltage. In first output amplifier 7 and I/V amplifier 8, heat associated with use is generated to cause a large drift in the system of measurement. Regarding the magnitude of the drift, variations in measured values are caused at a certain rate.

After step S2, warm-up signal computing unit 27 of warm-up section 22 computes a warm-up signal for warming up first output amplifier 7 and I/V amplifier 8 (S3).

In order to warm up the system of measurement to the extent that equals the magnitude of the drift determined in step S2, warm-up signal computing unit 27 computes the warm-up signal of the same current in magnitude as that which is to flow through measurement electrode 3 during the measurement.

The warm-up signal is one which causes first output amplifier 7 and I/V amplifier 8, which configure the system of measurement, to generate heat in the same state as during the measurement. Therefore, when the warm-up signal is set to an alternating current of 3 MHz equal in frequency to the bacteria-collection signal, warm-up signal computing unit 27 is expected to compute the amplitude of the warm-up signal.

In order to compute the amplitude, warm-up signal computing unit 27 starts by determining the magnitude of the current that is to flow through measurement electrode 3 during the actual measurement (during the application of the bacteria-collection signal), based on the solution conductivity determined in step S2.

Next, the warm-up signal computing unit computes the amplitude of the warm-up signal such that the current flowing through first output amplifier 7 and I/V amplifier 8 during the application of the warm-up signal is substantially equal in magnitude to the current that is to flow through first output amplifier 7 and I/V amplifier 8 during the measurement. Note that the amplitude can be appropriately computed and determined in consideration of the magnitude of load 36, through which the warm-up signal flows when applied from warm-up section 22.

This is because as follows: When applying the warm-up signal, the current thereof is caused to flow through load 25 without flowing through measurement electrode 3. Incidentally, the magnitude of the current which is to flow through measurement electrode 3 changes depending on the solution conductivity. Therefore, in order to cause the current to flow through load 25, with the current being the same in magnitude as the thus-changing current, warm-up signal computing unit 27 computes the amplitude of the warm-up signal in consideration of the magnitude of load 25.

After step S3, warm-up section 22 performs the warm-up (S4).

Here, warm-up signal generator 28 performs the warm-up of first output amplifier 7 and I/V amplifier 8, by using the warm-up signal generated in step S3. On this occasion, the warm-up is preferably performed in the state where measurement electrode 3 is not applied with the bacteria-collection signal (3 MHz, 10 Vpp). This also is the same as described in the first embodiment.

For this reason, in the embodiment, second warm-up switch 34 is disposed to selectively couple the output of first output amplifier 7 with any one of measurement electrode 3 and I/V amplifier 8. Then, a detour around measurement electrode 3 is configured with second warm-up switch 34, load 36, and adding-unit 35.

With this configuration, it is possible to apply the warm-up signal fed from warm-up section 22 to I/V amplifier 8 via first output amplifier 7 and the detour (second warm-up switch 34, load 36, and adding-unit 35) around measurement electrode 3. Accordingly, during the warm-up, measurement electrode 3 is not applied with the warm-up signal with the same magnitude of amplitude as that of the bacteria-collection signal. Accordingly, there is no decrease in measurement accuracy caused by the application of the warm-up signal to measurement electrode 3.

When performing the warm-up, firstly, first warm-up switch 33 is operated to select the warm-up section 22 side such that the output of warm-up section 22 is coupled with the input side of first output amplifier 7 via adding-unit 46. Next, the output side of second warm-up switch 34 is coupled with load 36 such that the output of first output amplifier 7 is coupled with the input side of I/V amplifier 8 via load 36 and adding-unit 35.

After that, warm-up signal generator 28 generates the warm-up signal (3 MHz) with the amplitude that has been computed by warm-up signal computing unit 27 in step S3.

Then, upon feeding the warm-up signal from warm-up section 22, the warm-up signal is applied to first output amplifier 7 via first warm-up switch 33 and adding-unit 46. The warm-up signal is further applied to I/V amplifier 8 as well, via second warm-up switch 34, load 36, and adding-unit 35.

On this occasion, it is possible to cause first output amplifier 7 and I/V amplifier 8 to generate heat in the same state as during the measurement, by feeding the measurement signal from measurement signal generator 5 simultaneously with the warm-up signal.

The warm-up is continuously performed for a certain period of time (e.g. 10 seconds).

With this configuration, for a period until the measurement is started, it is possible to cause first output amplifier 7 and I/V amplifier 8 to generate heat in the same state of the drift as during the measurement. Then, in the actual measurement, the measurement can be performed through the use of first output amplifier 7 and I/V amplifier 8 which have generated heat sufficiently, which thereby reduces the amount of the drift caused by heat generation during the measurement. Accordingly, this allows a reduction in variations in the drift caused by heat generation, resulting in a further increase in measurement accuracy.

Following step S4, the actual measurement for determining the number of microorganisms is then performed (S5).

First, first warm-up switch 33 is coupled with the bacteria-collection signal generator 4 side such that bacteria-collection signal generator 4 is coupled with first output amplifier 7 via adding-unit 46. Moreover, second warm-up switch 34 is coupled with the measurement electrode 3 side.

After that, adding-unit 46 adds the bacteria-collection signal voltage generated by bacteria-collection signal generator 4 and the measurement signal voltage generated by measurement signal generator 5. The thus-added voltage is fed to measurement electrode 3 via first output amplifier 7.

The application of the bacteria-collection signal voltage to measurement electrode 3 causes a dielectrophoretic force which collects, at measurement electrode 3, the microorganisms present in measurement liquid 2. Then, capacitance appears corresponding to the quantity of the microorganisms collected at measurement electrode 3. The value of the capacitance is, that is, the value of the impedance to be measured by impedance measuring unit 10.

Following step S5, operations of step S6 to step S8 are performed. Descriptions of each of the steps are the same as in the first embodiment.

Figure 6:
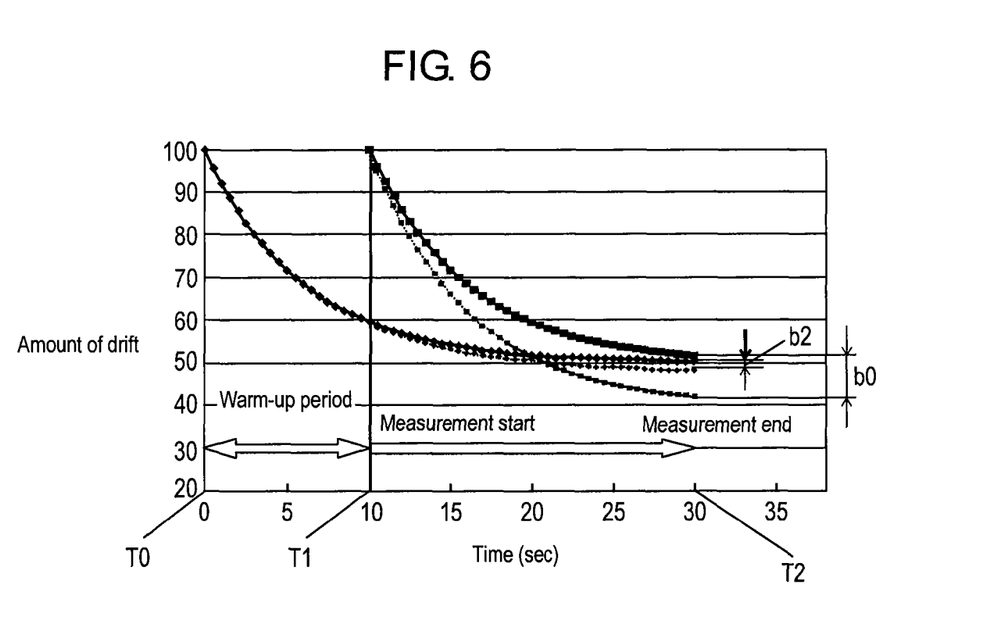
FIG. 6 is a graph illustrating variations in drifts when operating the microorganism number-measuring apparatus according to the second embodiment of the invention.

FIG. 6 is a graph illustrating variations in drifts when operating microorganism number-measuring apparatus 200 according to the second embodiment of the invention. FIG. 6 shows the changes with time in magnitude of the drifts of the system of measurement, which are derived using the theoretical equation under a certain condition, for the case where warm-up is performed and the case where no warm-up is performed.

As described above, in first output amplifier 7 and I/V amplifier 8, heat associated with use is generated. The heat causes a large drift of the system of measurement.

As shown in FIG. 6, the drifts settle into stable states with time in any of the cases. Associated with the drifts, variations in the measured values appear at a certain rate. Accordingly, the variations become large as the magnitude of the drifts (the amounts of the changes in impedance, from the initial impedance to the stable state impedance) becomes large. The variations possibly affect measurement accuracy.

A more specific description is made. As shown in FIG. 6, in the conventional cases, the drifts change for the period from actual-measurement starting time T1 (the amount of the drift: 100) to measurement ending time T2 (the amount of the drift: approximately 50). The amounts of the changes are so large that a large variation (b0) appears in the changes in the drifts.

In contrast, in microorganism number-measuring apparatus 200 according to the embodiment, the warm-up described in steps S2 to S4 is performed for the period of time from T0 to T1 (the preheating warm-up period), before starting the actual measurement. Through the warm-up, first output amplifier 7 and I/V amplifier 8 are caused to generate heat before the measurement, in the same state as during the measurement.

Accordingly, in the case of FIG. 6, the amounts of the drifts can be reduced to 60 at actual-measurement starting time T1.

Therefore, compared with the case where the no warm-up is performed, the changes in the amounts of the drifts can be made small for the period from actual-measurement starting time T1 (the amount of the drift: 60) to measurement ending time T2 (the amount of the drift: 50), which allows a remarkably reduced variation (b2) in the drifts. The variation in the drifts is smaller than variation (b1) in the drifts described in the first embodiment. The reason of this is considered that, in the embodiment, the warm-up is performed for first output amplifier 7 as well as I/V amplifier 8.

Moreover, in microorganism number-measuring apparatus 200 according to the embodiment, the warm-up is performed using the warm-up signal that has been computed by warm-up section 22. Therefore, it is possible to accurately predict the state of the drift (the ending point of the drift) at the time when the warm-up is finished.

Therefore, in the embodiment as well, the ending point of the drift caused by the warm-up can be set as a starting point of the drift to be caused by the measurement. Accordingly, in the measurement, microorganism number-computing unit 13 is allowed to perform an appropriate correction corresponding to the drift-changing, which thereby allows an increase in measurement accuracy.

As a result, use of microorganism number-measuring apparatus 200 according to the embodiment permits a further increase in measurement accuracy.

Figure 7:
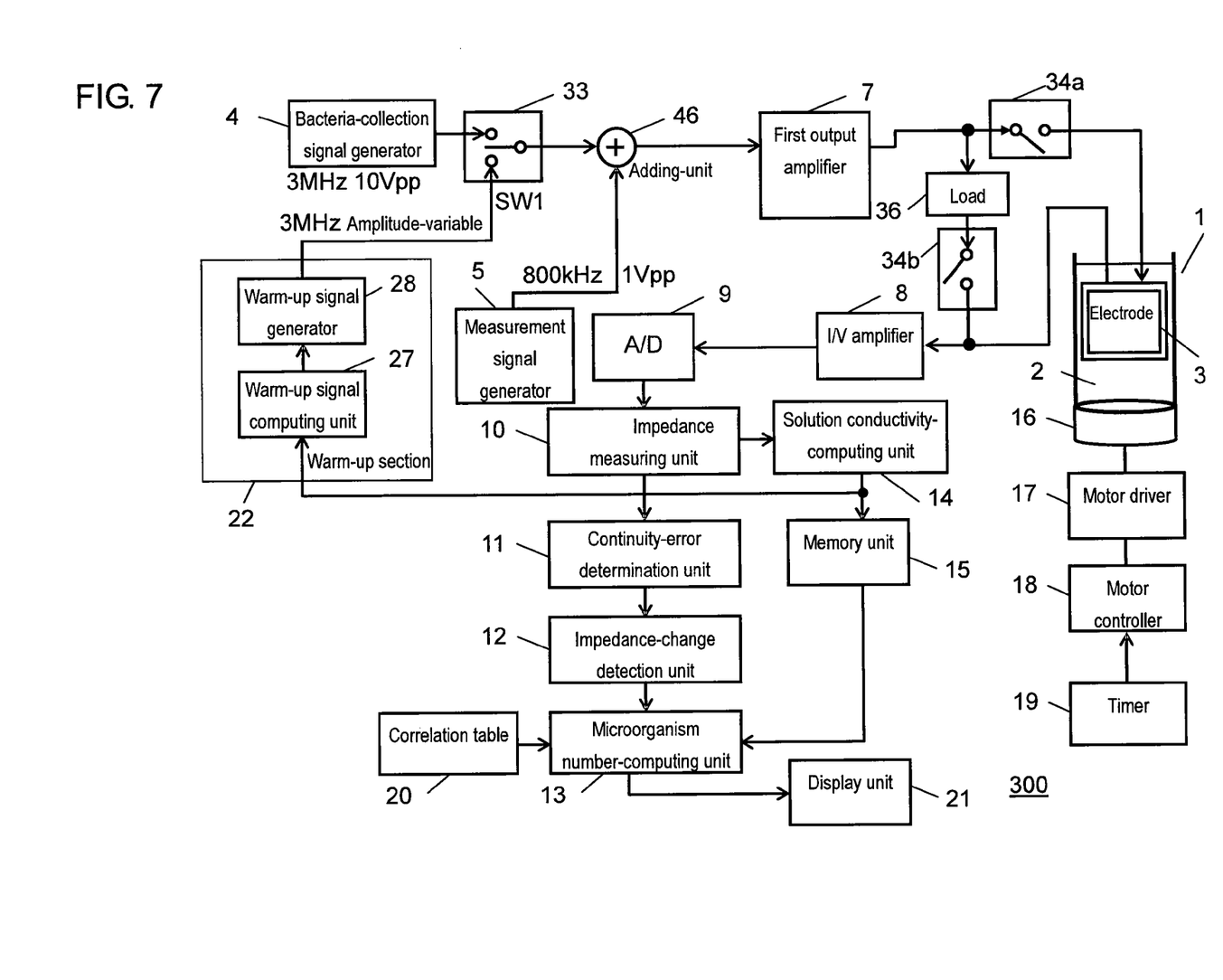
FIG. 7 is a block diagram of another configuration of the microorganism number-measuring apparatus according to the second embodiment of the invention.

FIG. 7 is a block diagram of another configuration of microorganism number-measuring apparatus 300 according to the second embodiment of the present invention.

In microorganism number-measuring apparatus 200 shown in FIG. 5, second warm-up switch 34 is configured such that the output of first output amplifier 7 is switched and fed to measurement electrode 3 or load 36. In microorganism number-measuring apparatus 300 shown in FIG. 7, the function of second warm-up switch 34 is configured to use two switches (warm-up switch 34a and warm-up switch 34b).

That is, the output of first output amplifier 7 is coupled with measurement electrode 3 via warm-up switch 34a. The input side of warm-up switch 34b is coupled, via load 36, with a point between output amplifier 7 and warm-up switch 34a. Then, the output side of warm-up switch 34b is coupled with a point between measurement electrode 3 and I/V amplifier 8.

In this configuration, when performing the warm-up in the measurement setup mode, warm-up switch 34a is turned OFF to couple the output of output amplifier 7 with the load 36 side, while warm-up switch 34b is turned ON to couple the output of the amplifier with I/V amplifier 8.

Since, during the warm-up, this configuration allows a detour around measurement electrode 3, which is formed with load 36 and warm-up switch 34b, measurement electrode 3 is not applied with the warm-up signal that has the ability of collecting bacteria. Accordingly, there is no decrease in measurement accuracy caused by the application of the warm-up signal to measurement electrode 3.

It is to be noted that, although the aforementioned descriptions in the embodiments have been made by using the exemplary cases where microorganism number-measuring apparatuses 100, 200, and 300 measure the number of microorganisms present inside an oral cavity, the present invention is not limited to these exemplary cases. For example, the present invention is applicable to a microorganism number-measuring apparatus that measures microorganisms present in food.

INDUSTRIAL APPLICABILITY

As described above, the present invention has the outstanding advantages of further increasing measurement accuracy. Therefore, for example, it is useful for such as a microorganism number-measuring apparatus that measures the number of microorganisms or the like, present inside an oral cavity or in food.

REFERENCE MARKS IN THE DRAWINGS 1 measurement container
2 measurement liquid
3 measurement electrode
4 bacteria-collection signal generator
5 measurement signal generator
6, 26, 35, 46 adding-unit
7 first output amplifier (output amplifier)
8 I/V amplifier
9 A/D converter
10 impedance measuring unit
11 continuity-error determination unit
12 impedance-change detection unit
13 microorganism number-computing unit
14 solution conductivity-computing unit
15 memory unit
16 motor (rotary driver)
17 motor driver
18 motor controller
19 timer
20 correlation table
21 display unit
22 warm-up section
23 second output amplifier
24, 34a, 34b warm-up switch
25, 36 load
27 warm-up signal computing unit 28 warm-up signal generator
33 first warm-up switch
34 second warm-up switch
100, 200, 300 microorganism number-measuring apparatus

The invention claimed is:

1. A microorganism number-measuring apparatus, comprising:
- a measurement container including a measurement liquid and an measurement electrode disposed in the liquid in an immersed state;
- a rotary driver for rotationally driving the measurement liquid in the measurement container;
- a bacteria-collection signal generator for feeding a bacteria-collection signal to the measurement electrode;
- a measurement signal generator for feeding a measurement signal to the measurement electrode;
- an output amplifier for amplifying an output of the measurement signal generator and an output of bacteria-collection signal generator;
- an I/V amplifier coupled with an output of the output amplifier via the measurement electrode;
- an impedance measuring unit coupled with the I/V amplifier, the measuring unit measuring impedance of the measurement liquid;
- a microorganism number-computing unit coupled with the impedance measuring unit, the number-computing unit computing a number of microorganisms present in the measurement liquid;
- a solution conductivity-computing unit coupled with the impedance measuring unit, the conductivity-computing unit computing an electric conductivity of the measurement liquid; and
- a warm-up section for performing warm-up of at least one of the I/V amplifier and the output amplifier, the solution conductivity-computing unit being coupled with the warm-up section, an output of the warm-up section being coupled with at least one of the I/V amplifier and the output amplifier via a warm-up switch, wherein, in a measurement setup mode, the solution conductivity-computing unit measures a solution electric conductivity of the measurement liquid, the warm-up section computes a warm-up signal by using the measured solution electric conductivity, the warm-up signal having a current identical in magnitude to a current flowing through the measurement electrode, and the warm-up section performs the warm-up by applying the warm-up signal to at least one of the I/V amplifier and the output amplifier.

2. The microorganism number-measuring apparatus according to claim 1, wherein the rotary driver rotationally drives the measurement container.

3. The microorganism number-measuring apparatus according to claim 1, wherein the warm-up section includes:
- a warm-up signal computing unit for computing the warm-up signal; and
- a warm-up signal generator coupled with an output side of the warm-up signal computing unit.

4. The microorganism number-measuring apparatus according to claim 3, wherein the warm-up signal generator computes the warm-up signal, the warm-up signal being an alternating current with a frequency substantially identical to a frequency of the bacteria-collection signal generated by the bacteria-collection signal generator.

* * * * *